(12) United States Patent
Iwase et al.

(10) Patent No.: US 10,102,621 B2
(45) Date of Patent: Oct. 16, 2018

(54) APPARATUS, METHOD, AND PROGRAM FOR PROCESSING IMAGE

(71) Applicant: CANON KABUSHIKI KAISHA, Tokyo (JP)

(72) Inventors: Yoshihiko Iwase, Yokohama (JP); Makoto Sato, Tokyo (JP); Akihito Uji, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 65 days.

(21) Appl. No.: 15/121,339

(22) PCT Filed: Feb. 24, 2015

(86) PCT No.: PCT/JP2015/056024
§ 371 (c)(1),
(2) Date: Aug. 24, 2016

(87) PCT Pub. No.: WO2015/129909
PCT Pub. Date: Sep. 3, 2015

(65) Prior Publication Data
US 2017/0018077 A1    Jan. 19, 2017

(30) Foreign Application Priority Data
Feb. 28, 2014 (JP) ................... 2014-038923

(51) Int. Cl.
*G06K 9/00* (2006.01)
*G06T 7/00* (2017.01)
(Continued)

(52) U.S. Cl.
CPC .......... *G06T 7/0012* (2013.01); *A61B 3/0025* (2013.01); *A61B 3/0033* (2013.01);
(Continued)

(58) Field of Classification Search
None
See application file for complete search history.

(56) References Cited

U.S. PATENT DOCUMENTS

2008/0225301 A1* 9/2008 Yamaguchi ........ G01B 9/02004
356/496
2012/0063660 A1* 3/2012 Imamura ............. A61B 5/0066
382/131
(Continued)

FOREIGN PATENT DOCUMENTS

CN     103578081 A    2/2014
JP     2013-34658 A   2/2013

OTHER PUBLICATIONS

Bolz, M., et al., "Optical Coherence Tomographic Hyperreflective Foci: A Morphologic Sign of Lipid Extravasation in Diabetic Macular Edema" Ophthalmology, May 2009, pp. 914-920, vol. 116, No. 5.

*Primary Examiner* — Hadi Akhavannik
(74) *Attorney, Agent, or Firm* — Canon USA Inc., IP Division

(57) ABSTRACT

A high-resolution image suited to the purpose of a doctor or the like is acquired. The present invention relates to an image processing apparatus including an acquisition unit configured to acquire a tomogram of a subject eye; a first extraction unit configured to extract part of the tomogram acquired by the acquisition unit; an estimating unit configured to estimate a high-frequency component based on a result of extraction by the extraction unit; and a combining unit configured to combine the high-frequency component with the tomogram acquired by the acquisition unit.

16 Claims, 16 Drawing Sheets

(51) Int. Cl.
    *A61B 3/10*           (2006.01)
    *G06T 5/00*           (2006.01)
    *G06T 7/13*           (2017.01)
    *A61B 3/00*           (2006.01)

(52) U.S. Cl.
    CPC ............ *A61B 3/0041* (2013.01); *A61B 3/102* (2013.01); *G06T 5/004* (2013.01); *G06T 7/13* (2017.01); *G06T 2207/10101* (2013.01); *G06T 2207/20192* (2013.01); *G06T 2207/30041* (2013.01)

(56) References Cited

U.S. PATENT DOCUMENTS

| | | | | |
|---|---|---|---|---|
| 2012/0083667 A1* | 4/2012 | Isogai | .................... | A61B 3/102 600/300 |
| 2012/0249962 A1* | 10/2012 | Uchida | ................. | A61B 3/102 351/208 |
| 2012/0250029 A1* | 10/2012 | Yoshida | ................. | A61B 3/102 356/497 |

* cited by examiner

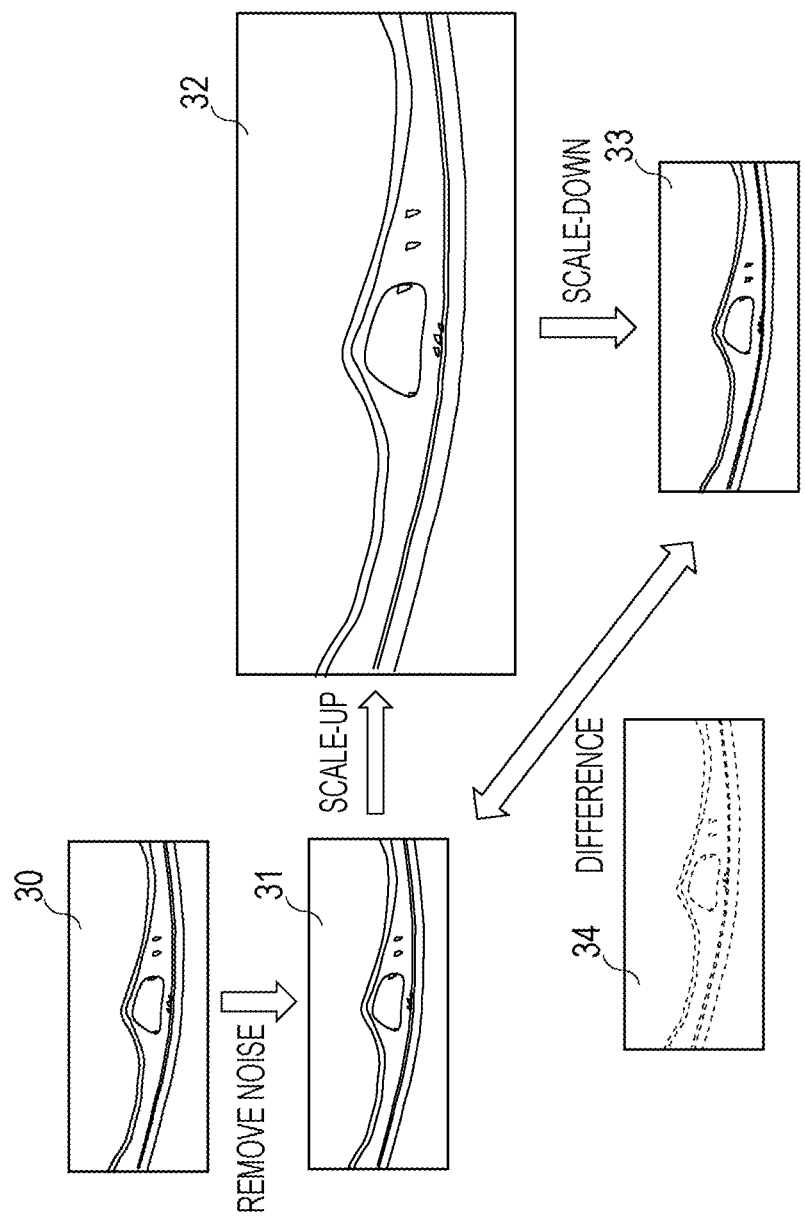

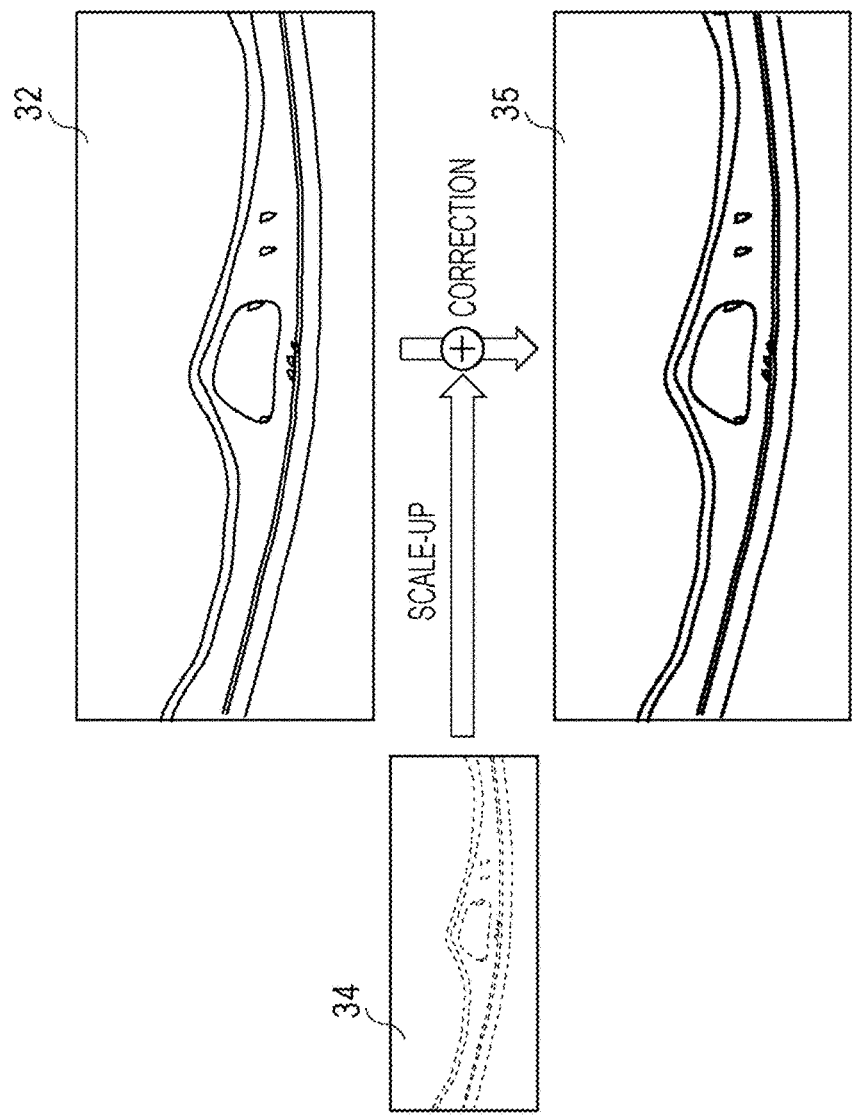

FIG. 9A
$\sigma_a$
$\sigma_a < \sigma_b$
FIG. 9B
$\sigma_b$
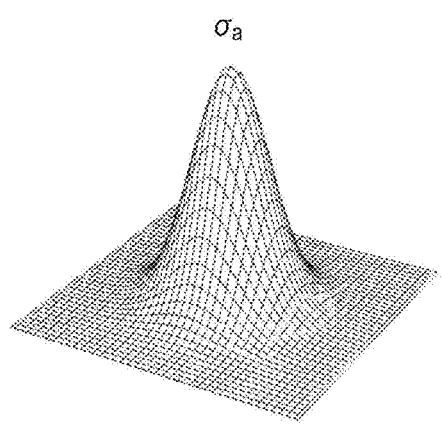
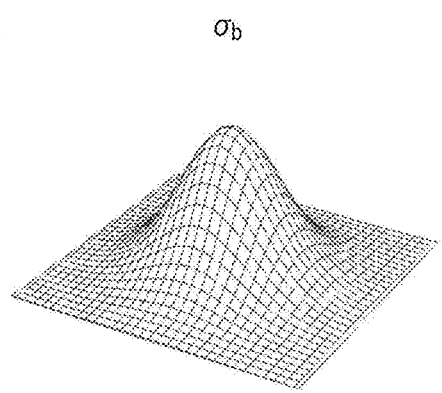
FIG. 9C
FIG. 9D
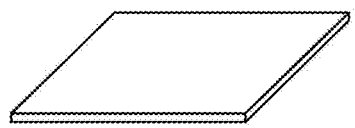
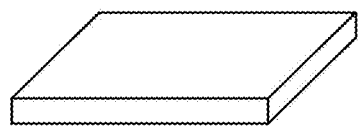

APPARATUS, METHOD, AND PROGRAM FOR PROCESSING IMAGE

TECHNICAL FIELD

The present invention relates to an apparatus, a method, and a program for processing an image.

BACKGROUND ART

Eye tomographs, such as an optical coherence tomograph (OCT), allow three-dimensional observation of the interior of a retinal layer. The tomographs have recently attracted attention because of the usefulness in correct disease diagnosis. An example of the OCT is a time domain OCT (TD-OCT) in which a broadband light source and a Michelson interferometer are combined. This OCT is configured to scan the delay of a reference arm to measure the interference of light with back-scattered light from a signal arm, thereby obtaining information on depth resolution. It is, however, difficult for such TD-OCT to achieve high-speed image acquisition. Thus, a spectral domain (OCTSD-OCT) configured to obtain an interferogram using a beam splitter and a broadband light source is known as a method for acquire images at higher speed. Another example of the OCT is a swept source OCT (SS-OCT) that employs a method of measuring spectral interference with a single-channel light detector by using a high-speed wavelength-swept light source.

Diagnosis using tomograms acquired by such OCTs requires high-quality tomograms. To this end, PTL 1 discloses a method for super-resolution processing to acquire clear images in tomography.

The degree of progression of a disease and the degree of recovery after treatment have conventionally been evaluated by checking the thickness of a retinal layer in a tomogram. However, according to NPL 1, the recent progress of the OCTs tends to improve pathological understanding on an observation target in a tomogram by evaluating not only the thickness of a retinal layer but also a small lesion.

CITATION LIST

Patent Literature

PTL 1 Japanese Patent Laid-Open No. 2013-34658

Non Patent Literature

NPL atthias Bolz, et al. "Optical Coherence Tomographic Hyperreflective Foci: A Morphologic Sign of Lipid Extravasation in Diabetic Macular Edema" Ophthalmology, 2009

SUMMARY OF INVENTION

Technical Problem

However, the super-resolution processing disclosed in PTL 1 is sometimes incorrect because the super-resolution processing is uniformly performed on all of a plurality of images.

The present invention is made in view of the above problem. The present invention generates a high-resolution tomogram by appropriate super-resolution processing on a tomogram. The present invention can also offer operational advantages attributed to configurations shown in the embodiments described below, which are not given by the relate art.

Solution to Problem

The present invention provides an image processing apparatus including an acquisition unit configured to acquire a tomogram of a subject eye; a first extraction unit configured to extract part of the tomogram acquired by the acquisition unit; an estimating unit configured to estimate a high-frequency component based on a result of extraction by the extraction unit; and a combining unit configured to combine the high-frequency component with the tomogram acquired by the acquisition unit.

Further features of the present invention will become apparent from the following description of exemplary embodiments with reference to the attached drawings.

BRIEF DESCRIPTION OF DRAWINGS

FIG. 3 is a diagram illustrating an example of a high-resolution processing.

FIG. 4 is a diagram illustrating an example of a high-resolution processing.

FIG. 9A is a diagram for explaining an example of the structural-object emphasizing process.

FIG. 9B is a diagram for explaining an example of the structural-object emphasizing process.

FIG. 9C is a diagram for explaining an example of the structural-object emphasizing process.

FIG. 9D is a diagram for explaining an example of the structural-object emphasizing process.

DESCRIPTION OF EMBODIMENTS

First Embodiment

A first embodiment will be described hereinbelow with reference to the drawings. An image processing system including an image processing apparatus according to the embodiment estimates a high-frequency component from an OCT image to generate a high-resolution image.

The details of the image processing system including the image processing apparatus according to the embodiment (image processing apparatus) will be described in detail hereinbelow.

Figure 1:
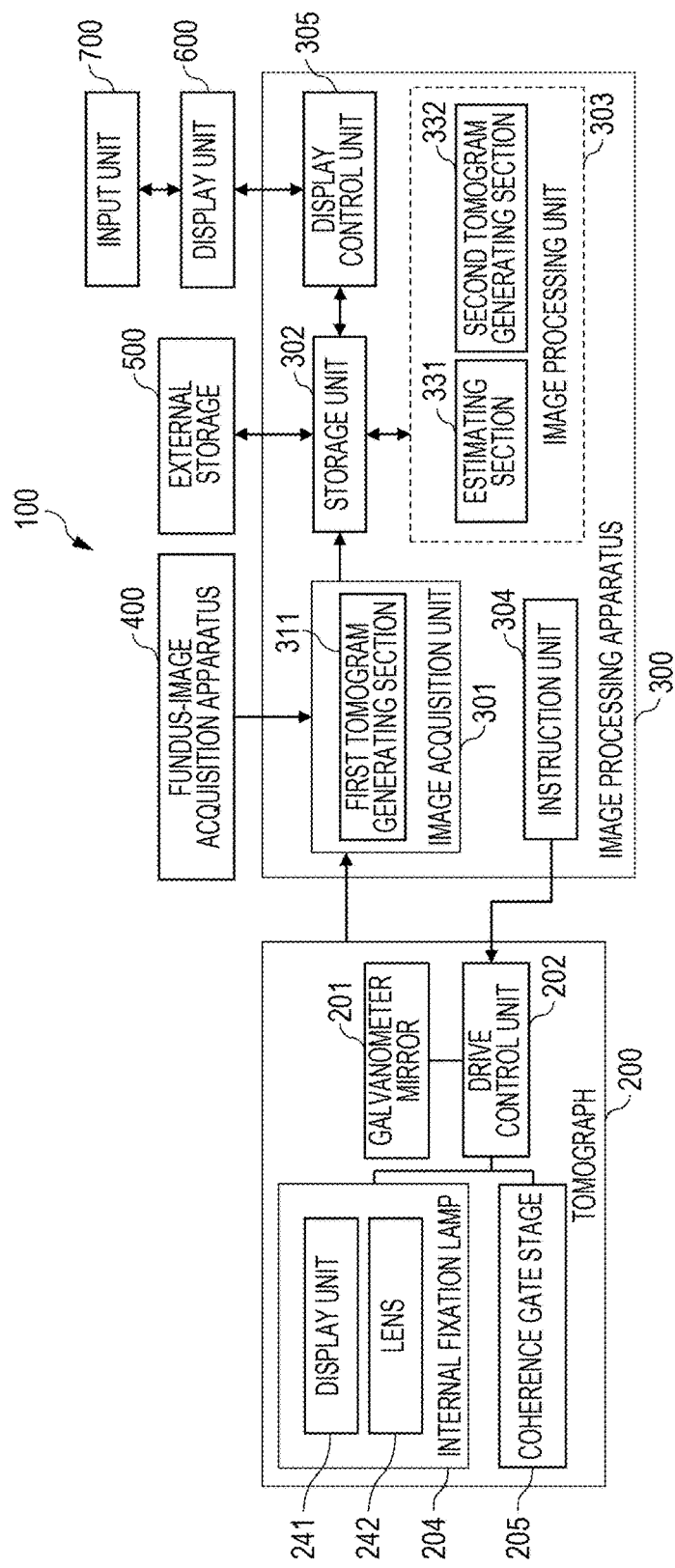
FIG. 1 is a diagram showing an example of the configuration of an image processing system according to a first embodiment.

FIG. 1 is a diagram showing the configuration of an image processing system 100 including an image processing apparatus 300 according to the embodiment. As shown in FIG. 1, the image processing system 100 is configured such that the image processing apparatus 300 is connected to a tomograph (also referred to as an OCT) 200, an ophthalmoscope 400, an external storage 500, a display unit 600, and an input unit 700 via an interface. The interface may be connected either by wire or wirelessly. Part of the functions of the image processing apparatus 300 in FIG. 1 may be disposed in the OCT 200, or alternatively, the image processing apparatus 300 and the OCT 200 may be combined together.

The tomograph 200 is an apparatus configured to acquire a tomogram of an eye. Examples of the tomograph 200 include an SD-OCT and an SS-OCT. Since the tomograph 200 is a known apparatus, a detailed description thereof will be omitted, and the image-acquisition area of the tomogram and setting of parameters of an internal fixation lamp 204 will be described here.

In FIG. 1, a galvanometer mirror 201 is a device for scanning the fundus with measurement light and defines the area of image acquisition of the fundus in OCT. A drive control unit 202 defines the image-acquisition area of the fundus in a planar direction and the number of scanning lines (a scanning speed in the planar direction) by controlling the driving area and speed of the galvanometer mirror 201. Although a single galvanometer mirror 201 is shown for clarity, the galvanometer mirror 201 is actually composed of two mirrors for X-direction scanning and Y-direction scanning, thus allowing a desired area of the fundus to be scanned with measurement light.

The internal fixation lamp 204 includes a display unit 241 and a lens 242. An example of the display unit 241 is a plurality of light-emitting diodes (LDs) in a matrix form. The light-emitting positions of the light-emitting diodes are changed depending on an image-acquisition site under the control of the drive control unit 202. The light from the display unit 241 is guided to a subject eye through the lens 242. The light emitted from the display unit 241 has, for example, a wavelength of 520 nm, and has a desired pattern under the control of the drive control unit 202. The wavelength of the light is given as example and is not limited to the above value.

A coherence gate stage 205 is controlled by the drive control unit 202 to cope with a difference in the axial length of the subject eye. The coherence gate indicates a position where the optical lengths of measurement light and reference light in the OCT are equal. Another method for image acquisition is enhanced depth imaging (hereinafter, referred to as EDI) in which the position of the coherence gate is at a retinal layer side or deeper in the retinal layer. In the image acquisition using the EDI method, the position of the coherence gate is set deeper in the retinal layer. Thus, this has the feature of allowing images of a choroid coat and a retinal pigment epithelium (RPE) to be acquired at higher brightness than a case where the coherence gate is located at the fundus side.

An ophthalmoscope 400 is an apparatus for acquiring an image of the fundus of an eye. Examples include a fundus camera and a scanning laser ophthalmoscope (SLO).

The image processing apparatus 300 includes an image acquisition unit 301, a storage unit 302, an image processing unit 303, an instruction unit 304, and a display control unit 305.

The image acquisition unit 301 includes a first tomogram generating section 311 to generate a tomogram by obtaining signal data on a tomographic image acquired by the tomograph 200 and performing signal processing thereon. That is, the image acquisition unit 301 corresponds to an example of an acquisition unit configured to acquire a tomogram of a subject eye. Specifically, the image acquisition unit 301, which is an example of the acquisition unit, acquires a tomogram of the fundus.

The first tomogram generating section 311 stores the generated tomogram in the storage unit 302. The image acquisition unit 301 acquires a two-dimensional front image (fundus image) acquired by the fundus-image acquisition unit 400.

The image processing unit 303 includes an estimating section 331 and a second tomogram generating section 332. The estimating section 331 estimates a high-frequency component from the tomogram generated by the first tomogram generating section 311. The high-frequency component is information on pixels not included in the tomogram generated by the first tomogram generating section 311.

The second tomogram generating section 332 generates a high-resolution tomogram from the high-frequency component estimated by the estimating section 331 and the tomogram created by the first tomogram generating section. In other words, the second tomogram generating section 332 increases the resolution of the tomogram. The high-resolution tomogram is, for example, an image with higher resolution than that of the tomogram created by the first tomogram generating section 311.

The instruction unit 304 gives instructions on image acquisition parameters and so on to the tomograph 200. For example, the instruction unit 304 gives instructions on various parameters, such as image acquisition parameters, input with the input unit 700 described below, to the tomograph 200. For example, the instruction unit 304 gives an instruction on the position of the internal fixation lamp 204 to the drive control unit 202.

The external storage 500 stores subject identification numbers and information on a subject eye (the name, age, sex, and so on of the patient), and various items of data, such as acquired image data, image-acquisition parameters, image analysis parameters, and parameters set by the operator, in association with each other.

Examples of the input unit 700 include pointing devices, such as a mouse, a keyboard, and a touch screen. The operator gives an instruction to the image processing apparatus 300, the tomograph 200, and the ophthalmoscope 400 via the input unit 700. Although the input unit 700 and the display unit 600 in FIG. 1 are directly connected together, the present invention is not limited thereto; the input unit 700 may be connected to the image processing apparatus 300.

Figure 2A:
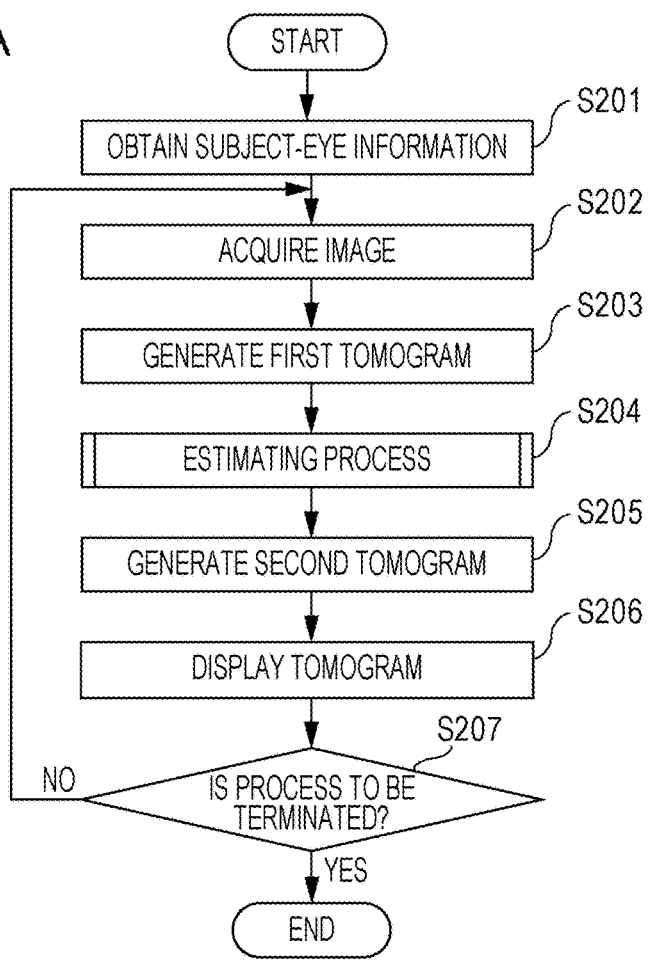
FIG. 2A is a flowchart of an example of the operation of the image processing system according to the first embodiment.
Figure 2B:
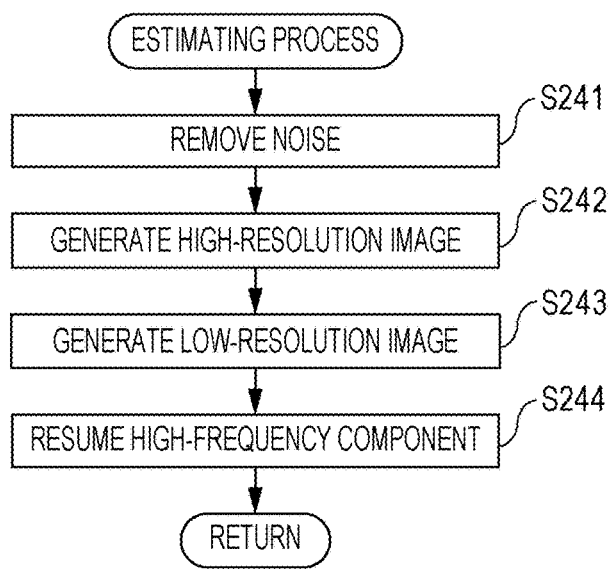
FIG. 2B is a flowchart of an estimating process of the image processing system according to the first embodiment.

Referring next to FIGS. 2A and 2B, the procedure of the image processing apparatus 300 of this embodiment will be described. FIG. 2A is a flowchart of the operation of the entire system (super-resolution process) of the embodiment.

Step S201

At step S201, for example, a subject-eye-information acquisition section (not shown) in the image processing apparatus 300 obtains a subject identification number from the exterior as information for identifying the subject eye. The subject-eye-information acquisition section obtains information on the subject eye stored in the external storage 500 on the basis of the subject identification number and stores the information in the storage unit 302. The step S201 corresponds to an example of an acquisition step.

Step S202

At step S202, image-acquisition parameters are set for image acquisition. Specifically, the position of the internal fixation lamp 204 and a scanning pattern are set.

The drive control unit 202 controls the light-emitting diodes of the display unit 241 and sets the position of the internal fixation lamp 204 so as to acquire an image at the center of a macula portion. This is for the purpose of acquiring an image of the vicinity of the central fovea related to eyesight. The scan pattern is set to, for example, 3D scanning or cross scanning.

The drive control unit 202 sets such image-acquisition parameters to acquire a tomogram of the subject eye. The tomograph 200 acquires a tomogram by operating the galvanometer mirror 201 with the drive control unit 202. The galvanometer mirror 201 includes an X-scanner for a horizontal direction and a Y-scanner for a vertical direction. Thus, changing the directions of these scanners allows scanning in the horizontal direction (X) and the vertical direction (Y) in the apparatus coordinate system. Changing the directions of the scanners at the same time allows scanning in a direction in which the horizontal direction and the vertical direction are combined, thus allowing scanning in any direction on the fundus plane.

Step S203

At step S203, the first tomogram generating section 311 acquires signal data on the tomographic image acquired by the tomograph 200 and processes the signals to generate a tomogram. A case where the SS-OCT is used as the tomograph 200 will be described. First, fixed noise is removed from the signal data. Next, the signal data is subjected to spectral shaping and dispersion compensation. The signal data is then subjected to discrete Fourier transform into depth-dependent intensity data. The first tomogram generating section 311 clips a desired area from the Fourier-transformed intensity data to generate a tomogram.

Step S204

At step S204, the estimating section 331 estimates a high-frequency component from the tomogram generated by the first tomogram generating section 331. The details of the method will be described with reference to FIG. 2B and FIG. 3.

Step S241

At step S241 in FIG. 2B, the estimating section 331 removes noise from a tomogram 30 (see FIG. 3) generated by the first tomogram generating section 311. The noise in the tomogram 30 is removed by applying averaging filtering, median filtering, or the like to the tomogram 30. Noise may be removed not only by filtering on one image but also acquiring a plurality of images of the same site and overlapping the plurality of tomograms (averaging).

Step S242

At step S242, the estimating section 331 scales up a tomogram 31 generated by removing noise at step S241 to generate a high-resolution tomogram 32. For example, if the size of the tomogram 31 is 1,024×512, it is scaled up to 2,048×1,024. An example of a method for interpolation in the scaling-up process is a bicubic method. Other methods for image interpolation are, in addition to the bicubic method, Lanczos2 interpolation and Lanczos3 interpolation. The image size described above is given as an example only and is not intended to limit the invention, and other values may be used.

Step S243

At step S243, the estimating section 331 scales down the tomogram 32 enlarged at step S242 to generate a low-resolution tomogram 33 (a reference image). When the pixel values of the low-resolution image are to be calculated, the low-resolution image can be generated by calculating the average value of the pixel values of the high-resolution tomogram corresponding to the area. Another method for generating a low-resolution image is to generate a tomogram with the same size as that of the first tomogram using the bicubic method. A process for scale-down is also not limited to the above method as in scale-up.

Step S244

At step S244, the estimating section 331 compares the input tomogram 31 and the tomogram 33 reduced in resolution after being increased in resolution in units of pixels to determine (estimate) a difference (high-frequency component). Thus, the estimating section 331 generates a tomogram 34 including a high-frequency component for restoring a high-resolution image. That is, the estimating section 331 corresponds to an example of a difference acquisition unit configured to obtain the difference between the reference image obtained by scaling up and down the tomogram acquired by the acquisition unit and the tomogram acquired by the acquisition unit. In other words, the estimating section 331 acquires a high-frequency component.

Although, at step S241 to S243, the tomogram 33 is generated in the order in which the image is scaled up and is then scaled down, the tomogram 33 may be generated in the order in which the image is scaled down and is then scaled up.

Step S205

At step S205, the second tomogram generating section 332 generates a high-resolution tomogram using the tomogram 34 that the estimating section 331 estimated at step S204. This method will be described with reference to FIG. 4. Step 205 corresponds to an example of a combination step.

In FIG. 4, the tomogram 32 and the tomogram 34 are tomograms generated at the estimating process at step S204. If the tomogram 34 is generated in the order in which the tomogram is scaled down and then scaled up during the resuming process, the tomogram 32 is not generated at step S204. In this case, at step S205, the estimating section 331 generates the tomogram 32 scaled up from the tomogram 31.

The second tomogram generating section 332 scales up the tomogram 34 including a high-frequency component into the same size as that of the tomogram 32 and adds the high-frequency component to the tomogram 32. Thus, a high-resolution tomogram 35 can be obtained.

Step S206

Figure 5:
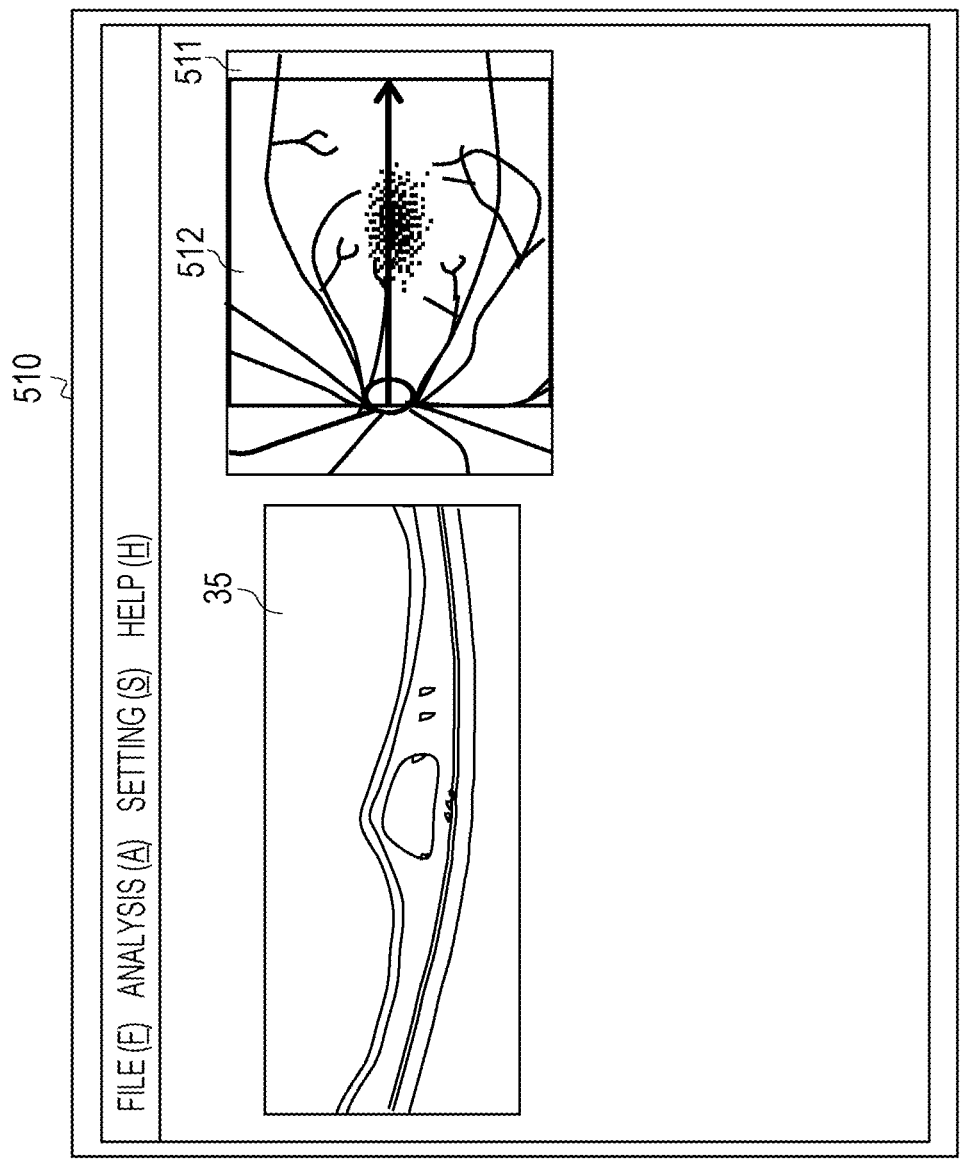
FIG. 5 is a diagram illustrating a display example of the result of analysis.

At step S206, the display control unit 305 displays the tomogram 35 generated by the second tomogram generating section 332 on the display unit 600. FIG. 5 shows a display example.

In this embodiment, the high-resolution tomogram 35 is displayed as a final output. FIG. 5 shows an example in which an image is acquired by 3D-scanning and the scan data is displayed. Reference sign 510 denotes a tomogram observation screen, 511 denotes a fundus image (in this embodiment, an SLO image), 512 denotes an image in which a scanning pattern is superimposed on the fundus image, and 35 denotes a high-resolution tomogram. The fundus image 511 is acquired by, for example, the image acquisition unit 301. Although the high-resolution tomogram 35 and the fundus image 511 in the display example shown in FIG. 5 are displayed in a lateral direction, the present invention is not limited thereto. For example, the display control unit 305 may display the tomogram 35 and the fundus image 511 in tandem.

Although not shown, a thickness map or thickness graph calculated by analyzing the thicknesses of layers in the tomogram may be displayed together. The display control unit 305 may display a tomogram generated by the first tomogram generating section 311 and a tomogram generated by the second tomogram generating section 332 on the display unit 600.

Step S207

At step S207, an instruction acquisition section (not shown) receives an instruction on whether to terminate the tomogram acquisition performed by the image processing system 100 from the exterior. This instruction is input by the operator with, for example, the input unit 700. If an instruction to terminate the process is given, the image processing system 100 terminates the process. In contrast, if the process is not to be terminated and is continued, the process is returned to step S202, and the image acquisition is continued.

Although, in the above embodiment, the process is terminated following a termination instruction from the input unit 700, the present invention is not limited thereto. For example, the process may be terminated when all of a plurality of (or a predetermined number of) tomograms acquired by three-dimensional scanning are subjected to the high-resolution processing described above.

Thus, the process of the image processing system 100 is performed.

The configuration described above allows fast processing speed because only one tomogram is used for processing and facilitates applying to a three-dimensional scanning pattern. Furthermore, the generation of the high-resolution image allows the boundary of a retinal layer and the boundary of a lesion to be emphasized. This makes it easy to view a precursor of hard white exudate, called hyperreflective foci, the internal structure of a cystic cavity, and so on of a diabetic macular edema. For a macular hole, a photoreceptor-cell inner-outer-segments joint portion adhering to a detached retina and the bottom of the hole can easily be viewed. These effects promote better understanding of disease, allowing the tomogram to be an index of early diagnosis of disease.

Furthermore, since eyes moves all the time due to involuntary eye movement or the like, it has been difficult to select a plurality of suitable tomograms to obtain a high-resolution tomogram from a plurality of tomograms. However, this embodiment does not have such difficulty. That is, this embodiment allows easier acquisition of a high-resolution tomogram. This facilitates acquiring a high-resolution tomogram of an eye whose fixation is unstable due to disease.

In other words, this embodiment allows a higher-resolution tomogram to be acquired by super-resolution processing suitable for increasing image processing speed to acquire a high-resolution tomogram in real time or for making a diagnosis without influence of involuntary eye movement.

Second Embodiment

The first embodiment shows an example in which the estimating section 331 estimates a high-frequency component of a tomogram to generate a second tomogram with high resolution. A second embodiment differs from the first embodiment in the process of estimating a high-frequency component performed by the estimating section 331 in FIG. 1 (step S204 in FIG. 2A). Since the other processes are the same as those of the first embodiment, descriptions thereof will be omitted.

Figure 6:
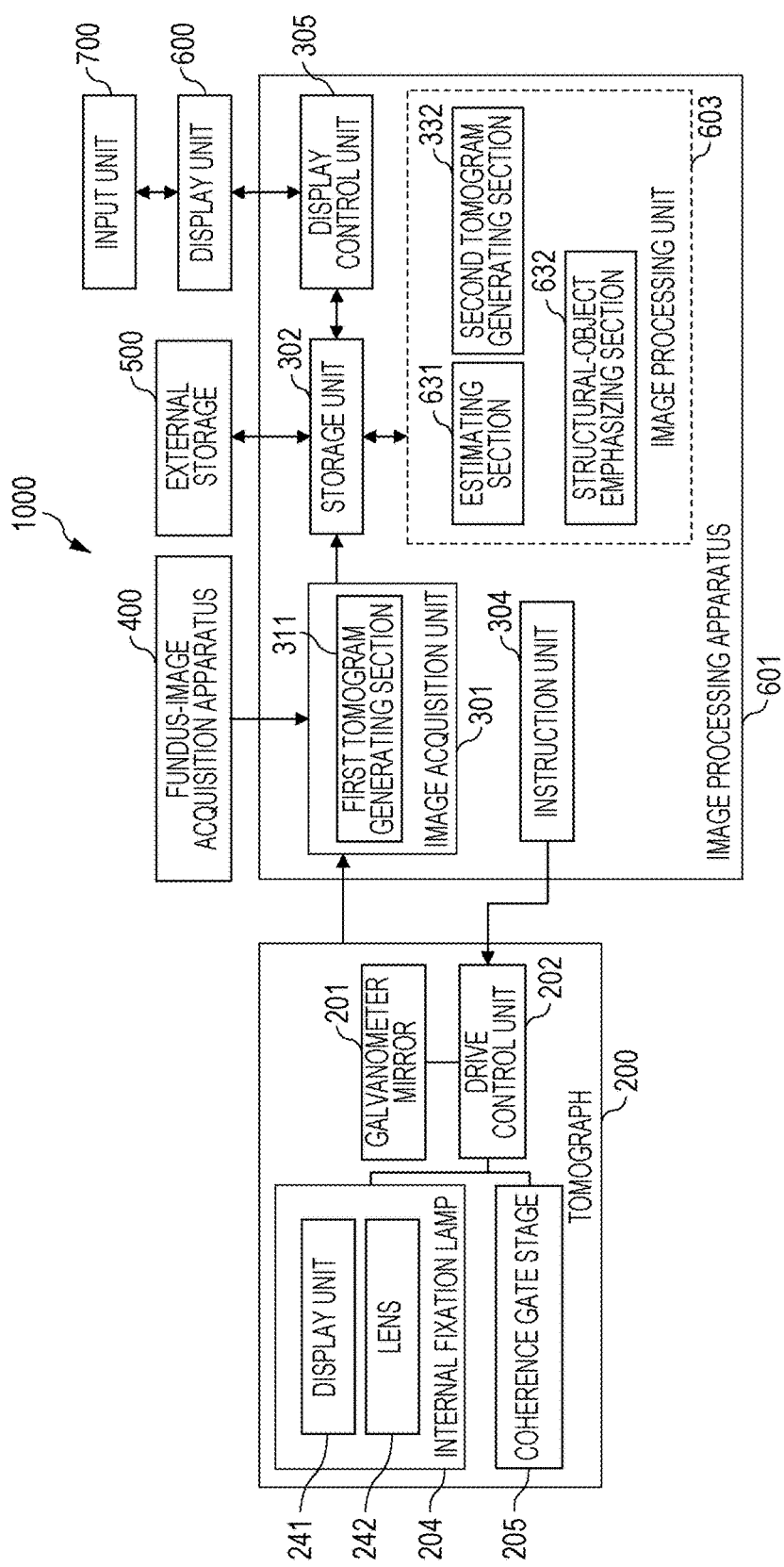
FIG. 6 is a diagram showing an example of the configuration of an image processing system according to a second embodiment.

FIG. 6 is a diagram showing the configuration of an image processing system 1000 including an image processing apparatus 601 according to the second embodiment. In this embodiment, an image processing unit 603 includes an estimating section 631, a structural-object emphasizing section 632, and a second tomogram generating section 332. The estimating section 631 estimates a high-frequency component in a tomogram on the basis of the structural characteristics of the tomogram emphasized by the structural-object emphasizing section 632. Some function of the image processing apparatus 601 in FIG. 6 may be provided in the OCT 200, or alternatively, the image processing apparatus 601 and the OCT 200 may be integrated.

Figure 7A:
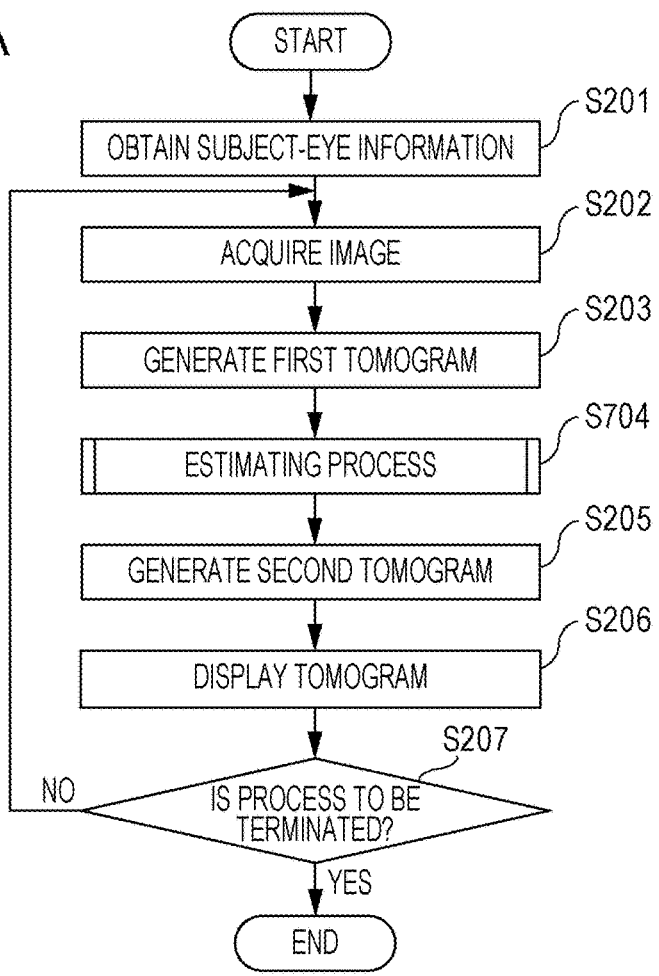
FIG. 7A is a flowchart of an example of the operation of the image processing system according to the second embodiment.
Figure 7B:
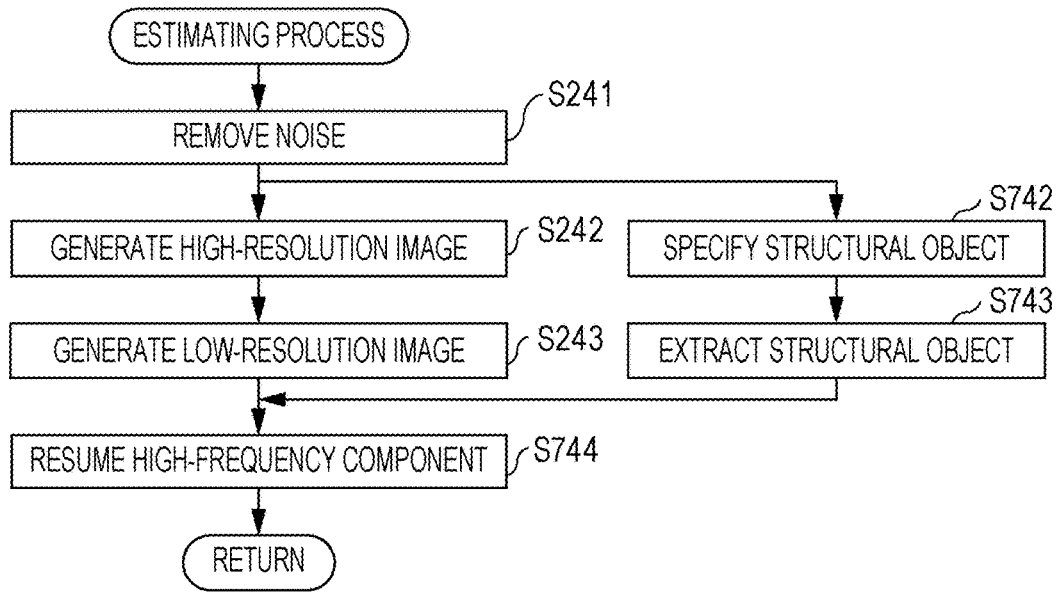
FIG. 7B is a flowchart of an estimating process of the image processing system according to the second embodiment.

FIGS. 7A and 7B show the procedure of the image processing apparatus 601 of this embodiment. FIG. 7A is a flowchart of the operation of the entire system of this embodiment. An estimating process at step S704 in FIG. 7A will be described with reference to FIG. 7B. In FIG. 7B, since steps S241 to S243 are the same as steps S241 to S243 in the first embodiment, descriptions thereof will be omitted. Since steps S201 to 203 in FIG. 7A are also the same as steps S201 to 203 in FIG. 2A, descriptions thereof will be omitted.

Step S742

At step S742, a structural object to be increased in resolution in the tomogram is specified. Examples of the structural object in the tomogram include a layer structure (a layer boundary), a granular structure, and a vascular structure. The structural object to be increased in resolution is not limited to the above examples, and any other structural objects are possible.

The second embodiment will be described as applied to a case where a layer structure is specified as an example of the structural object. The structural object to be emphasized is specified using, for example, initial setting or a user interface. For a revisiting patent, the same structure as that of a structure emphasized at the previous diagnosis may be emphasized on the basis of information thereon stored in the storage unit 302. In the case where a disease name of a patient can be extracted from medical information, such as an electronic medical record, a structure corresponding to the disease name may be emphasized. This can be achieved by preparing a table in which disease names and structures to be emphasized are associated. For example, a layer structure is emphasized for glaucoma because the layer thickness is an important factor.

Step S743

At step S743, the structural-object emphasizing section 632 emphasizes a layer structure. Step S743 corresponds to an example a first extraction step. This embodiment shows a case where a layer is recognized from three-dimensional data acquired by 3D scanning. The description is made on the assumption that alignment of adjacent B-scan data in three-dimensional data composed of a plurality of items of B-scan data has been completed.

The following description is for a case where a layer-structure emphasis filter based on eigenvalues of the Hessian matrix is used to emphasize the layer structure of a retina. Specifically, a secondary local structure of a three-dimensional concentration distribution can be emphasized on the basis of the relationship among three eigenvalues ($\lambda_1, \lambda_2, \lambda_3$) of the Hessian matrix.

Figure 8:
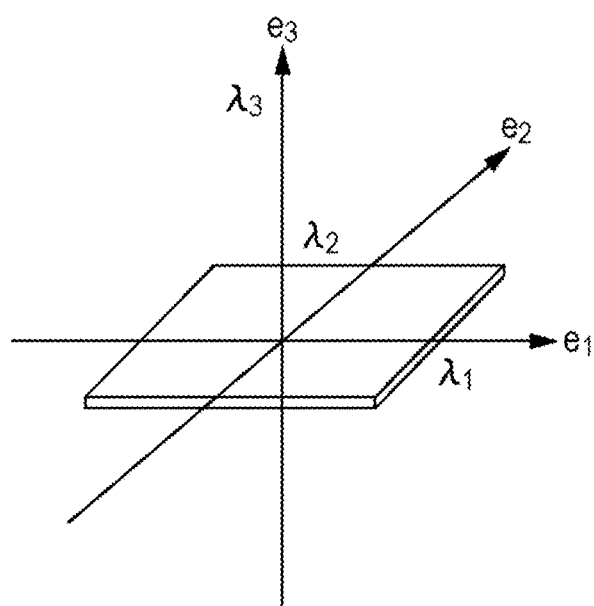
FIG. 8 is a diagram for explaining an example of a structural-object emphasizing process.

The Hessian matrix can be given by Math. 1. The Hessian matrix is a square matrix made of all the two-stage partial derivatives of a function of many variables, where I is the gray value of the image. FIG. 8 shows the relationship between the eigenvalues of the Hessian matrix and eigenvectors ($e_1, e_2, e_3$) in the case where a layer structure is emphasized. Math. 2 shows the relationship among the eigenvalues of the Hessian matrix, and Math. 3 shows a conditional expression of the eigenvalues that emphasize a layer structure.

$$H = \begin{pmatrix} I_{xx} & I_{xy} & I_{xz} \\ I_{yx} & I_{yy} & I_{yz} \\ I_{zx} & I_{zy} & I_{zz} \end{pmatrix}$$  [Math. 1]

$$\lambda_3 \le \lambda_2 \le \lambda_1$$ [Math. 2]
$$\lambda_3 \le \lambda_2 \le \lambda_1$$

$$\lambda_3 << \lambda_2 = \lambda_1 = 0$$ [Math. 3]

By calculating Math. 4 using the thus-obtained three eigenvalues, the layer structure of the retina can be emphasized.

$$S_{sheet}\{f\} = \begin{cases} |\lambda_3| \cdot \omega(\lambda_2; \lambda_3) \cdot \omega(\lambda_1; \lambda_3) & \lambda_3 < 0 \\ 0 & \text{otherwise} \end{cases}$$ [Math. 4]

where $\omega(\lambda_s; \lambda_t)$ is a weighting function, which is shown in Math. 5.

$$\omega(\lambda_s; \lambda_t) = \begin{cases} \left(1 + \frac{\lambda_s}{|\lambda_t|}\right)^\gamma & \lambda_t \le \lambda_s \le 0 \\ \left(1 - \alpha \frac{\lambda_s}{\lambda_t}\right)^\gamma & \frac{|\lambda_t|}{\alpha} > \lambda_s > 0 \\ 0 & \text{otherwise} \end{cases}$$ [Math. 5]

where $\gamma$ and $\alpha$ are weighting functions.

Furthermore, a layer-structure emphasis filter with multiresolution can be used to cope with retinal layers with various thicknesses. To this end, the eigenvalues of the Hessian matrix for a smoothed image using a Gaussian function G (x; $\sigma_f$) with a plurality of resolutions $\sigma_f$ may be analyzed, where x is (x,y,z). FIGS. 9A and 9B show Gaussian functions with different resolutions $\sigma_f$, and FIGS. 9C and 9D show images of the thicknesses of layers emphasized using them, respectively. FIG. 9C shows the thickness of a layer emphasized using the Gaussian function in FIG. 9A, and FIG. 9D shows the thickness of a layer emphasized using the Gaussian function in FIG. 9B. The resolution of the Gaussian function in FIG. 9A is $\sigma_a$, and the resolution of the Gaussian function in FIG. 9B is $\sigma_b$. The relationship between the two resolutions is expressed by Math. 6.

Next, the expression of a smoothed image using Gaussian functions is shown in Math. 7. Math. 7 expresses one component in the Hessian matrix, and the other components can also be obtained by Math. 7. By setting a plurality of resolutions $\sigma_f$ in Math. 7, and solving Math. 1 and Math. 4 with the individual resolutions, retinal layers with thicknesses corresponding to the individual resolutions can be emphasized.

Math. 8 is an expression for integrating the results of the use of the plurality of resolutions $\sigma_f$. This allows coping with retinal layers with various thicknesses using one output. The multiplier $\sigma_i^2$ is put in Math. 8 to perform a normalization process, where i is 1 to n, which corresponds to the number n of the set resolutions.

$$\sigma_a < \sigma_b$$ [Math. 6]

$$I_{xx} = \frac{\partial^2}{\partial x^2} G(x; \sigma_f) * I(x)$$ [Math. 7]

$$S_{sheet}(x) = \max_i \{\sigma_i^2 S_{sheet}(x; \sigma_i)\}$$ [Math. 8]

Although the process of integrating a plurality of resolutions $\sigma_f$ using Math. 8 has been described here, there is no need to necessarily integrate them. The results of processing using resolutions suitable for the thicknesses of the layers may be stored and be used for the individual layers.

Figure 10:
FIG. 10 is a diagram for explaining an example of the structural-object emphasizing process.

Although a description that the layer structure of a retina is emphasized using the eigenvalues of the Hessian matrix has been made using Math. 4 and Math. 5, the present invention is not limited to those expressions provided that the layer structure is emphasized using the relationship among the eigenvalues. Although the Hessian matrix is used to emphasize the layer structure, the present invention is not limited thereto. A Sobel filter or the like may be used to emphasize a boundary. In the case where the Sobel filter is used, the layer structure may be emphasized using a horizontal mask and a diagonal mask as shown in FIG. 10 because a retinal layer in a tomogram is curved with reference to the horizontal direction.

The granular structure and the vascular structure may be emphasized using the eigenvalues of the Hessian matrix similarly to the layer structure. In this case, a conditional expression of eigenvalues for emphasizing the granular structure is Math. 9, and a conditional expression of eigenvalues for emphasizing the vascular structure is Math. 10.

$$\lambda_3 = \lambda_2 = \lambda_1 << 0$$ [Math. 9]

$$\lambda_3 = \lambda_2 << \lambda_1 = 0$$ [Math. 10]

Although a description is given for the case of three-dimensional data, the present invention is not limited to the three-dimensional data. The above process is applicable also to two-dimensional data, in which case the number of dimensions may be decreased by one for calculation. The above process is also effective, in tomogram acquisition scanning, on scanning patterns in which adjacent B-scan data are discrete, such as cross scanning and radial scanning. In a two-dimensional tomogram, however, a granular structure and a vascular structure are observed in the form of circles, and a layer structure is observed in the form of a line. Although the granular structure and the vascular structure are observed in the form of similar circles, the size of the observation target differs between the granular structure, such as hyperreflective foci, and blood vessels. Thus, a resolution based on the Gaussian function may be set to the size of an object to be emphasized. Detection of the granular structure and blood vessels is not limited thereto; a circular form may be detected using Hough transform, for example.

That is, the structural-object emphasizing section 632 corresponds to a first extraction unit configured to detect part of the tomogram acquired by the acquisition unit.

The layer boundary, the granular structure (granular object), and the vascular structure extracted at step S743 are regions for use in medical diagnosis. In other words, the first extraction unit extracts a region for use in diagnosis as part of the tomogram acquired by the acquisition unit. More specifically, the structural-object emphasizing section 632 corresponding to an example of the first extraction unit extracts at least one of a layer boundary and a granular object as part of the tomogram acquired by the acquisition unit.

Step S744

At step S744, the estimating section 631 estimates a high-frequency component on the basis of the structure emphasized by the structural-object emphasizing section 632.

Figure 11:
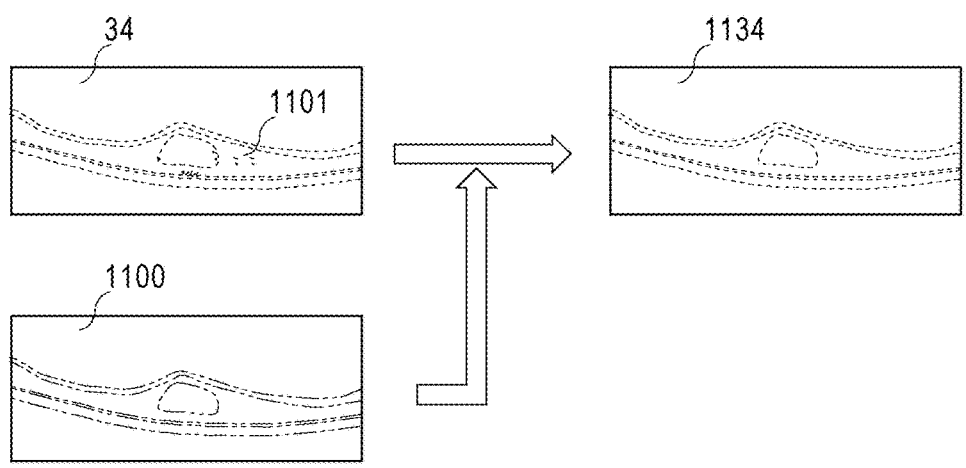
FIG. 11 is a diagram for explaining an example of a high-resolution process.

Step S744 corresponds to an example of an estimating step. Referring to FIG. 11, a process of generating a tomogram including a high-frequency component of a specific structural object will be described. In FIG. 11, the tomogram 34 is a tomogram including a high-frequency component created in the same way as at step S204. A tomogram 1100 is a tomogram generated by the structural-object emphasizing section 632 in which the specific structural object is emphasized. In other words, the tomogram 1100 is the tomogram acquired at step S743. FIG. 11 shows an example in which a layer structure is emphasized.

Although a granular structure 1101 is also detected in the tomogram 34 as a high-frequency component, the granular structure is not emphasize in the tomogram 1100 in which a layer structure is emphasized. Thus, using the tomogram 1100 in which a layer structure is emphasized allows a tomogram 1134 including a layer-structured high-frequency component to be generated.

A method for generating the tomogram 1134 will be described. When converting the tomogram 34 to the tomogram 1134, the estimating section 631 refers to the pixel values of the individual pixels at the same coordinate position in the tomogram 1100. In the tomogram 1100, high values are output to pixels at a location corresponding to the layer structure. Thus, if a pixel value of the tomogram 1100 is equal to or greater than a threshold value T, a value of the tomogram 34 (an example of a difference obtained by the difference acquisition unit) is output as it is, and if the value is smaller than the threshold value T, the value is set to 0. This allows the tomogram 1134 including a layer-structured high-frequency component to be generated. That is, the estimating section 631 corresponds to an example of an estimating unit configured to resume a high-frequency component on the basis of the result of extraction by the extraction unit. Specifically, the estimating section 631, which is an example of the estimating unit, estimates a high-frequency component on the basis of a difference obtained by the difference acquisition unit and the extraction result. The estimating section 631, which is an example of the estimating unit, estimates a high-frequency component on the basis of the result of extraction by the extraction unit in the tomogram acquired by the acquisition unit.

Although a weight assigned to the values of the tomogram 34 according to the values of the tomogram 1100 is set to a binary, 0 or 2, the present invention is not limited thereto. A weight assigned to the values of the tomogram 34 may be smoothly changed between 0 and 1 depending on the values of the tomogram 1100. Assume that a value of the tomogram 1100 is between 0 and 100. When a value of the tomogram 1100 is 100, a weight assigned to a value of the tomogram 34 is set to 1; when a value of the tomogram 1100 is 50, a weight assigned to a value of the tomogram 34 is set to 0.5; and when a value of the tomogram 1100 is 0, a weight assigned to a value of the tomogram 34 is set to 0. In other words, for one pixel, when the value of the tomogram 1100 is 100, the value of the tomogram 34 is output as it is; when the value of the tomogram 1100 is 50, a value obtained by multiplying the tomogram 34 by 0.5 is output; and when the value of the tomogram 1100 is 0, 0 is output.

Although this embodiment is described as applied to a case in which a layer structure is emphasized, the present invention is not limited thereto. Only a granular structure or only a vascular structure may be emphasized, or alternatively, a plurality of structural objects may be emphasized, like a layer structure+a granular structure. In other words, at least one of a layer structure, a granular structure, and a vascular structure is emphasized.

Furthermore, in the case where the location of a layer boundary is determined in combination with segmentation, only a desired layer, such as the whole of the inner layer of a retina or only a visual cell layer, may be subjected to high-resolution processing.

The second tomogram generating section 332 generates a high-resolution tomogram using the layer-structured tomogram 1134 including the high-frequency component estimated by the estimating section 631 at step S704. This process is the same as that in the first embodiment. That is, the second tomogram generating section 322 corresponds to an example of a combining unit configured to combine a high-frequency component with the tomogram acquired by the acquisition unit.

The tomogram that the second tomogram generating section 322 generates is not limited to one. A plurality of high-resolution tomograms in which at least one of a layer structure, a granular structure, and a vascular structure is emphasized may be generated.

For example, the second tomogram generating section 322, which is an example of the combining unit, generates a first processed image by combining a high-frequency component estimated on the basis of a layer boundary with the tomogram acquired by the acquisition unit and generates a second processed image by combining a high-frequency component estimated on the basis of a granular object with the tomogram acquired by the acquisition unit. The processed image is a tomogram increased in resolution, for example.

The display control unit 305 causes the thus-generated high-resolution tomogram to be displayed on the display unit 600. That is, the display control unit 305 corresponds to an example of a display control unit configured to cause a tomogram in which a high-frequency component is combined on a display unit. The number of the high-resolution tomogram displayed by the display control unit 305 is not limited to one; a plurality of tomograms may be displayed. For example, the display control unit 305 may cause a high-resolution tomogram in which a layer boundary is emphasized and a high-resolution tomogram in which a granular object is emphasized to be displayed on the display unit 600.

With the above configuration, the same advantageous effects as those of the first embodiment can be obtained, and in addition, the generation of the high-resolution image allows the boundary of a retinal layer and the boundary of a lesion to be emphasized. This makes it easy to view a precursor of hard white exudate, called hyperreflective foci, the internal structure of a cystic cavity, and so on of a diabetic macular edema. For a macular hole, a photoreceptor-cell inner-outer-segments joint portion adhering to a detached retina and the bottom of the hole can easily be viewed. These effects promote better understanding of disease, allowing the tomogram to be an index of early diagnosis of disease.

For example, noise in some tomogram generated by the first tomogram generating section is emphasized when the tomogram is increased in resolution even after noise is removed, thus interfering with determination of a target structural object. However, this embodiment increases the resolution depending on a structural object to be emphasized, thereby facilitating determining a target structural object.

That is, this embodiment allows a high-resolution tomogram to be acquired by super-resolution processing suitable for emphasizing mostly a predetermined structure on which doctors or the like focus attention.

Third Embodiment

The first and second embodiments show examples in which a high-resolution image is generated using one image. In a third embodiment, a process for generating a higher-resolution image using a plurality of high-resolution images shown in the first and second embodiments. Since the configuration of an image processing system of this embodiment is the same as that of FIG. 1 or 6, a detailed description will be omitted.

Figure 12A:
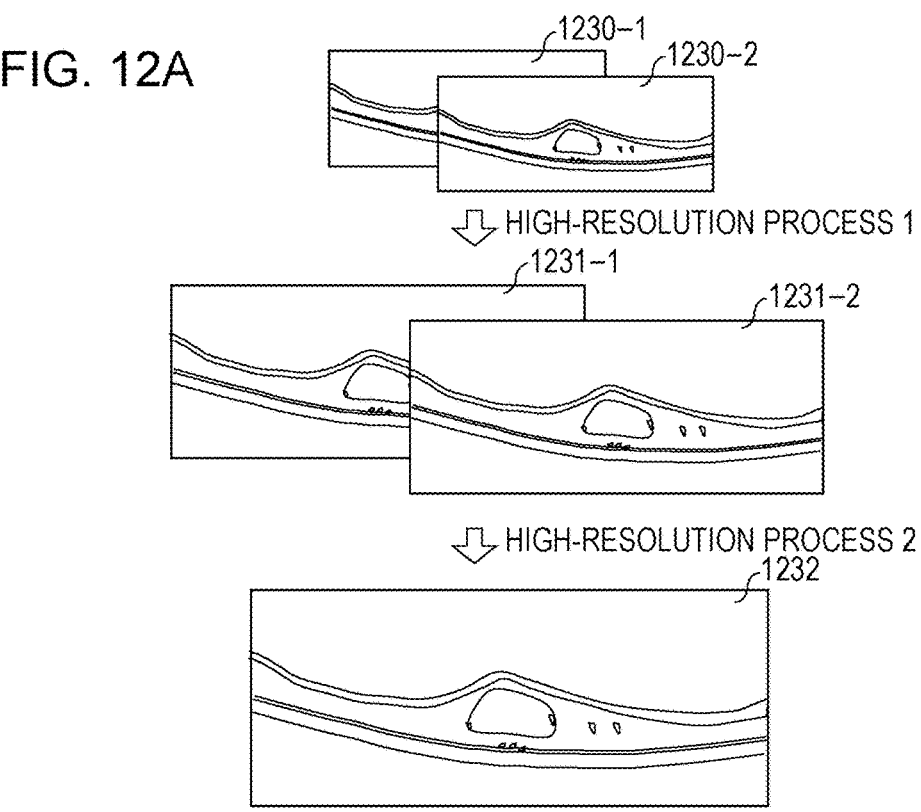
FIG. 12A is a diagram for explaining an example of a high-resolution process.

The process of this embodiment will now be described with reference to FIGS. 12A and 12B. In FIG. 12A, tomograms 1230-1 and 1230-2 are tomograms of an identical region acquired a plurality of times. The term "identical" is a concept including "substantially identical". In other words, regions from which the tomograms are acquired are not exactly identical due to involuntary eye movement or the like can also be regarded as an identical tomogram acquisition region. Any scanning method of acquiring tomograms of an identical region at different times can be employed in the present invention. Cross scanning, radial scanning, or 3-D scanning which allows a retinal layer to be scanned in three dimensions, may be employed provided that a three-dimensional image can be acquired by changing the scanning position while acquiring a plurality of tomograms of an identical region.

Tomograms 1231-1 and 1231-2 generated by a high-resolution process 1 shown in FIG. 12A are tomograms that are increased in resolution by the method shown in the first or second embodiment. That is, the high-resolution process 1 of this embodiment is a process of estimating a high-frequency component in a tomogram to generate a high-resolution tomogram. In the example, the tomograms 1231-1 and 1231-2 may be high-resolution images in which only a specific structural object, such as a layer structure or a granular structure, is emphasized. Alternatively, the tomograms 1231-1 and 1231-2 may be subjected to different processes; for example, the tomogram 1231-1 is a high-resolution image in which a layer structure is emphasized, and the tomogram 1231-2 is a high-resolution image in which a granular structure is emphasized. Alternatively, the tomograms 1231-1 and 1231-2 may be high-resolution images in which a plurality of structural objects are emphasized, such as a layer structure and a granular structure.

Since the high-resolution process 1 has been described in the first and second embodiments, a detailed description will be omitted.

A tomogram 1232 generated by a high-resolution process 2 is a high-resolution image generated from the plurality of high-resolution tomograms 1231-1 and 1231-2. In this embodiment, a process performed by the second tomogram generating section 332 will be described.

The second tomogram generating section 332 calculates the amount of misalignment of subpixels in a plurality of tomograms (in this embodiment, 1231-1 and 1231-2). The amount of misalignment of subpixels can be calculated using, for example, phase only correlation. The phase only correlation is a method for calculating the amount of misalignment of two images using phase information obtained through Fourier transform of the images.

Figure 12B:
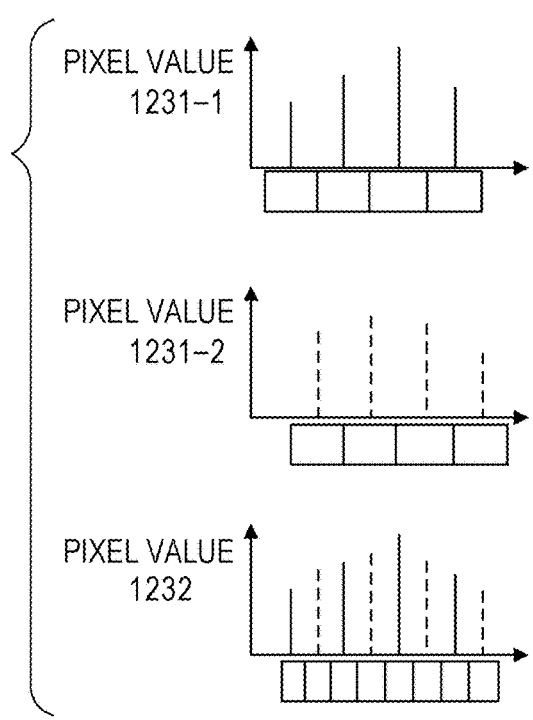
FIG. 12B is a diagram for explaining an example of the high-resolution process.

FIG. 12B shows some pixel values of the tomograms 1231-1, 1231-2, and 1232. The vertical axis indicates the pixel values of the tomograms 1231-1, 1231-2, and 1232, and the number of vertical lines indicates the pixels of the tomograms 1231-1, 1231-2, and 1232. Interpolating the pixel values of the tomograms 1231-1 and 1231-2, which are out of phase by a subpixel, allows the high-resolution tomogram 1232 to be generated. In other words, the second tomogram generating section 332 combines the subpixel-shifted tomograms 1231-1 and 1231-2. The second tomogram generating section 332 corresponds to an example of an image combining unit configured to combine a plurality of tomograms in which high-frequency components are combined by the combining unit.

Although this embodiment has been described as applied to a high-resolution process on two tomograms, the number of tomograms is not limited to two; three or more tomograms may be used. For example, four tomograms may be used.

Although this embodiment has been described as applied to an example in which a super-resolution process is performed on one image in the high-resolution process 1, and a super-resolution process on a plurality of images is performed in the high-resolution process 2, the order may be reversed. That is, a super-resolution process on a plurality of images may be performed in the high-resolution process 1, and a super-resolution process on one image may be performed in the high-resolution process 2.

With the above configuration, the same advantageous effects as those of the first and second embodiments can be offered, and in addition, a higher-resolution tomogram can be generated because one tomogram is created on the basis of a plurality of tomograms that are increased in resolution. Thus, the boundary of a retinal layer and the boundary of a lesion can be emphasized. This makes it easy to view a precursor of hard white exudate, called hyperreflective foci, the internal structure of a cystic cavity, and so on of a diabetic macular edema. For a macular hole, a photoreceptor-cell inner-outer-segments joint portion adhering to a detached retina and the bottom of the hole can easily be viewed. These effects promote better understanding of disease, allowing the tomogram to be an index of early diagnosis of disease.

Fourth Embodiment

In the above embodiments, methods for estimating a high-frequency component from an OCT image to generate a high-resolution image are described. In a fourth embodiment, a method for displaying the tomograms generated in the above embodiments will be described.

Figure 13A:
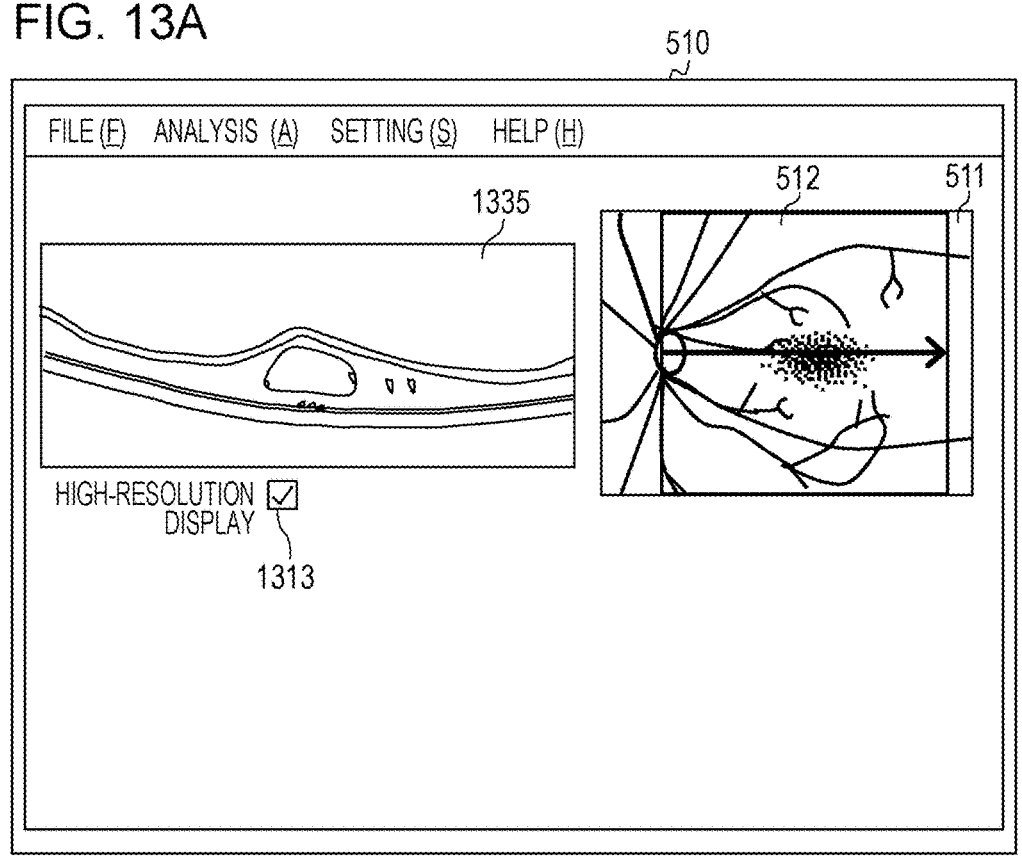
FIG. 13A is a diagram illustrating a display example of the result of analysis.

FIGS. 13A and 13B to FIG. 15 show display examples. In FIG. 13A, descriptions of the same portions as those in FIG.

5 will be omitted. FIG. 13A includes a checkbox 1313 for switching between ON and OFF of display of a high-resolution image, thus allowing the display to be switched at the same region. For example, the display control unit 305 determines whether to display a high-resolution tomogram 1335 on the display unit 600 on the basis of a flag indicating whether the checkbox 1313 is checked. The switching means is not limited to the checkbox 1313 but may be a radio button or a button. If the high-resolution display is ON, the high-resolution tomogram 1335 is displayed, and if the high-resolution display is OFF, an original tomogram (a tomogram acquired by the first image acquisition unit 311) is displayed.

This allows selective display at the same region, thus facilitating grasping a change before and after application of the high-resolution process.

Figure 13B:
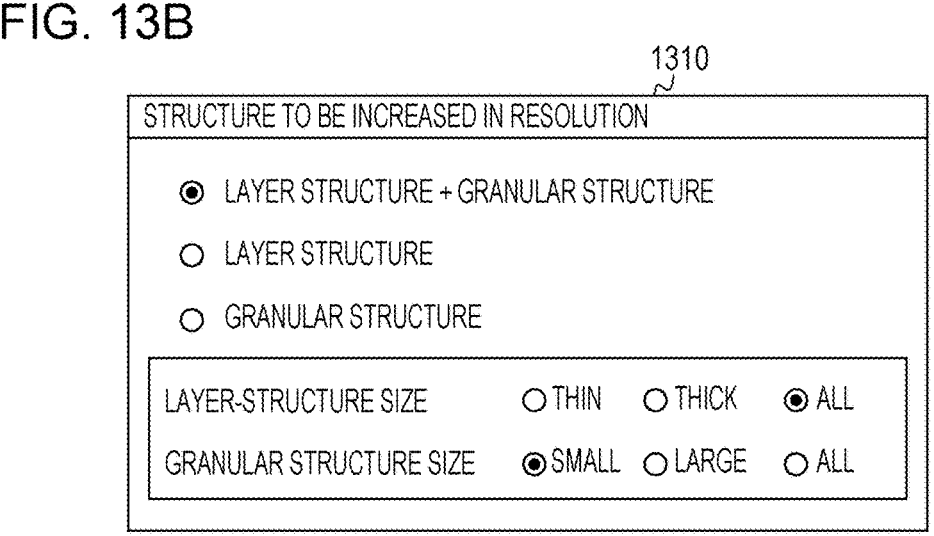
FIG. 13B is a diagram showing an example of a structure selection screen.

FIG. 13B shows an example of a screen for selecting a structure whose resolution is to be increased in the tomogram 1335 and the size thereof. This screen may be displayed via a setting menu for the tomogram observation screen 510. A structure selection screen 1310 shown in FIG. 13B shows an example in which a layer structure and a granular structure are selected. This setting menu allows the operator to select a structural object to be increased in resolution. Although the example shown in FIG. 13B shows, as structures, only a layer structure and a granular structure, the present invention is not limited thereto; another structural object may be selected.

In the example shown in FIG. 13B, three patterns, "thin layer structure", "thick layer structure", and "all layers", can be selected as the size of the layer structure. Similarly, three patterns, "small", "large", and "all", can be selected as the size of the granular structure. Although this embodiment has three choices for the size of the high-resolution structures, the present invention is not limited thereto; four or more choices may be prepared, or two choices may be provided.

For example, the structural-object emphasizing section 632 changes the resolution of Gaussian functions depending on the size of a selected layer structure and the size of a selected granular structure to change the high-resolution tomogram 1335 displayed on the display unit 600.

Figure 14:
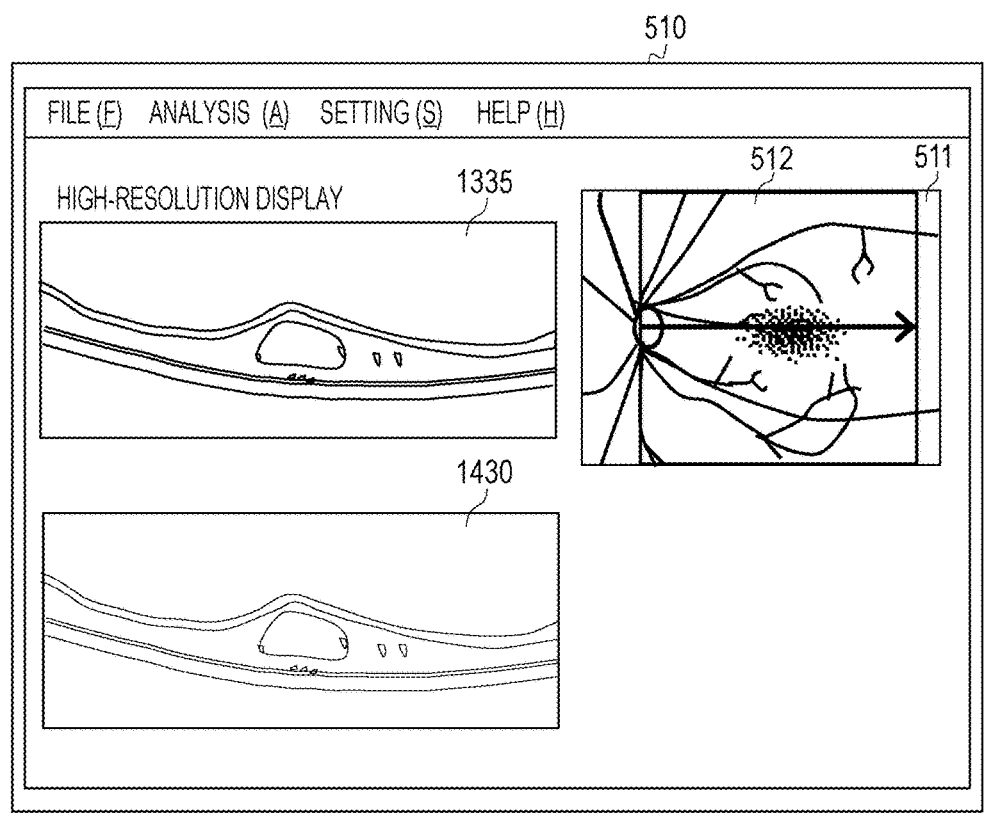
FIG. 14 is a diagram illustrating a display example of the result of analysis.

FIG. 14 shows the high-resolution tomogram 1335 and an original tomogram 1430 in a tiled manner. The tomogram 1430 is a tomogram acquired by, for example, the first tomogram generating section 311. In other words, the display control unit 305 corresponding to an example of the display control unit, causes a tomogram in which high-frequency components are combined and a tomogram acquired by the acquisition unit to be displayed on the display unit. Specifically, as shown in FIG. 14, the tomogram in which high-frequency components are combined and the tomogram acquired by the acquisition unit are displayed on the display unit in a tile manner. This allows an image subjected to a high-resolution process and an original image to be compared at the same time.

When the display positions of the tomograms 1335 and 1430, which are three-dimensional scanning patterns, are changed, both the tomograms 1335 and 1430 are changed in synchronization. Although FIG. 14 shows a tomogram at the center of three-dimensional data passing across a central fovea, tomograms having a different value of the three-dimensional data may be displayed. For example, when a position higher than a macular region in the fundus image 511 is designated by the input unit 700, the tomograms 1335 and 1430 in which a region above the macular region in the same fundus image 511 are acquired and displayed. Basically, a plurality of tomograms obtained by performing different processes on one tomogram are displayed, with the positions in synchronization, but the present invention is not limited thereto. For example, selecting a synchronization cancellation setting (not shown) allows the tomograms 1335 and 1430 of different regions to be displayed. At the time, indices indicating the locations of the tomograms 1335 and 1430 are displayed on the fundus image 511.

Specifically, two arrows are displayed on the fundus image 511 in FIG. 14, and the positions thereof correspond to the tomograms 1335 and 1430, respectively. In the case where positional information corresponding to the tomograms 1335 and 1430, such as arrows, is displayed, which of the tomograms 1335 and 1430 the positional information indicates may be clearly shown by employing different display forms for the positional information. For example, one of the two arrows is set to a dotted line, and the other is set to a solid line. The number of high-resolution tomograms displayed in FIG. 14 is not limited to one but may be more than one. For example, the display control unit 305 may cause a high-resolution tomogram in which a layer boundary is emphasized and a high-resolution tomogram in which a granular object is emphasized to be displayed on the display unit 600. The display positions of the plurality of high-resolution tomograms may be either synchronized or not synchronized. Furthermore, if the display positions are not synchronized, the display control unit 305 may cause arrows (positional information) corresponding to the acquisition positions of the individual high-resolution tomograms to be displayed on the fundus image 511.

In the example shown in FIG. 14, the tomogram 1430 is displayed below the high-resolution tomogram 1335. This is for illustration only and is not intended to limit the present invention. The display control unit 305 may display the tomogram 1430 above the high-resolution tomogram 1335. That is, the layout of the display screen is not limited to the example in FIG. 14 and may be changed. When displaying the high-resolution tomogram 1335 and the original tomogram 1430, the display control unit 305 displays information allowing the high-resolution tomogram 1335 to be identified. In the example shown in FIG. 14, the caption "high-resolution display" is displayed in the vicinity of the high-resolution tomogram 1335. This makes it easy for doctors to determine which is the high-resolution tomogram 1335. Instead of displaying the caption "high-resolution display", information that allows identification of an original image, such as a caption "original image display", may be displayed. Both of "high-resolution display" and "original image display" may be displayed.

Figure 15:
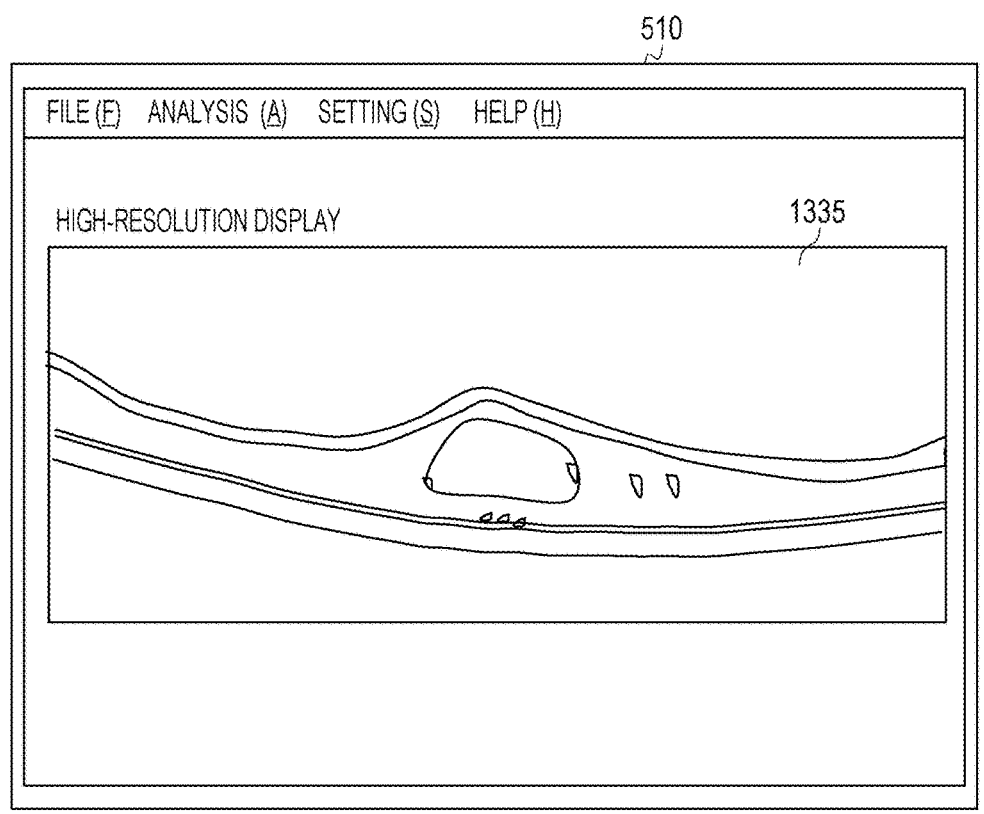
FIG. 15 is a diagram illustrating a display example of the result of analysis.

FIG. 15 displays the tomogram 1335 subjected to high-resolution processing in an enlarged view. This makes it easy to view even a small structural object because it is displayed at high resolution. For example, when the high-resolution tomogram 1335 in FIG. 13 or 14 is double-clicked, the display control unit 305 may shift the screen to a screen in FIG. 15. Although FIG. 15 does not show the fundus image 511, it may be displayed in a space in the tomogram observation screen 510 to allow the position of the enlarged tomogram 1335 to be determined.

Figure 16A:
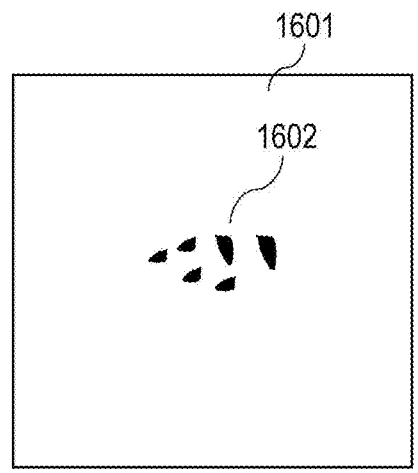
FIG. 16A is a diagram illustrating a display example of the result of analysis.
Figure 16B:
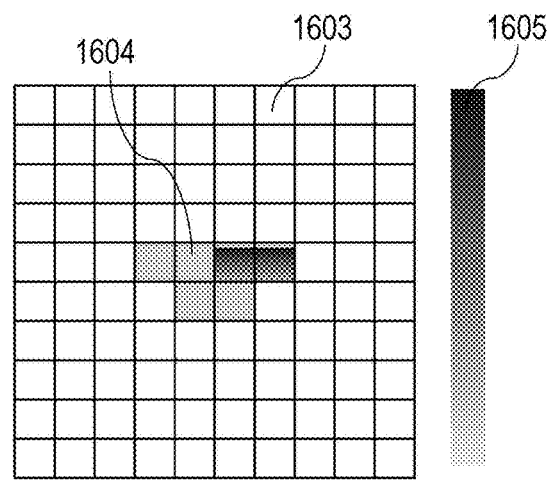
FIG. 16B is a diagram illustrating a display example of the result of analysis.
Figure 16C:
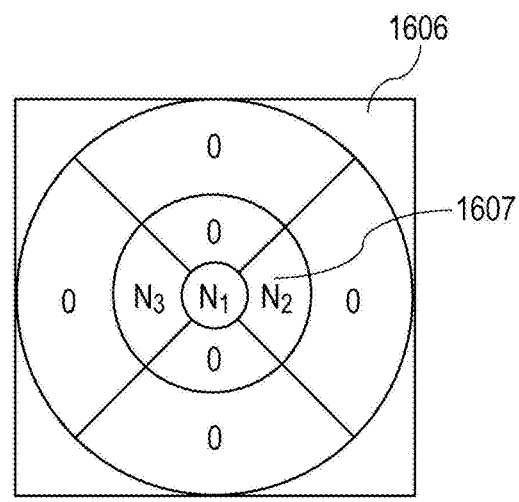
FIG. 16C is a diagram illustrating a display example of the result of analysis.

FIGS. 16A to 16C show examples in which a granular region is detected from a tomogram increased in resolution, and the detected granular region is displayed in the form of three-dimensional maps. The granular structure can be detected using the method described in the second embodiment. A layer boundary may be extracted from the high-resolution tomogram. There is no need to always extract both the layer boundary and the granular object; one of them may be detected. The extraction of the layer boundary and the granular region is performed by, for example, the image processing unit 303 or 603. That is, the image processing unit 603 corresponds to an example of a second extraction unit configured to extract at least one of a layer structure and a granular object from a tomogram in which a high-frequency component is combined.

FIG. 16A shows an example in which detected structural objects are displayed on a two-dimensional plane as an analysis map. In FIG. 16A, reference sign 1601 denotes an image-acquisition area in 3D-scanning image acquisition, showing the area of a map created by the image acquisition. Reference sign 1602 denotes detected granular structural objects.

In FIG. 16B, reference sign 1603 denotes an analysis map which is partitioned into squares with a given size. Reference sign 1604 denotes an example in which the percentage of granular structural objects in each square is expressed in color. Reference sign 1605 denotes a color scale bar in the case of color display (a monochrome scale bar is possible). In FIG. 16B, when the percentage in the area is high, it is displayed in dark color, and when the percentage in the area is low, it is displayed in light color. The color does not need to be monochrome; it is possible to use red for a high percentage, green for a low percentage, and gradation for an area therebetween. In other words, the display control unit 305 controls the display so that the percentage of granular structural objects in a partitioned area can be viewed.

In FIG. 16C, reference sign 1606 denotes an example of an analysis map partitioned by a combination of circles and straight lines. Reference signs $N_1$ to $N_3$ in 1607 indicate the number of granular structural objects present in one area. The above example in which the percentage of granular structural objects in the individual partitioned areas in the map is displayed in color and the example in which the percentage is indicated numerically are given for illustration and are not intended to limit the present invention. For example, the size of the granular structural objects may be expressed in color, numerically, or with a combination thereof.

All the maps in FIGS. 16A to 16C may be displayed on the display unit 600 at the same time, or alternatively, any of the maps in FIGS. 16A to 16C may be selectively displayed on the display unit 600.

The map shown in FIG. 16A shows the number, size, and distribution of granular objects. The map shown in FIG. 16B shows the distribution of granular objects, and the map shown in FIG. 16C shows the number and distribution of granular objects. In other words, to create these maps, the image processing unit 603, which is an example of the second extraction unit, extracts at least one of the number, size, and distribution of granular objects from the tomogram in which a high-frequency component is combined. Furthermore, as shown in FIGS. 16A to 16C, at least one of the number, size, and distribution of granular objects is displayed on the display unit 600 under the control of the display control unit 305. That is, the display control unit 305 corresponds to an example of a display control unit configured to cause at least one of the number, size, and distribution of granular objects to be displayed on the display unit.

These analysis maps may be displayed as they are, or alternatively, may be displayed over a fundus image (not shown) or an integrated image (pseudo scanning laser ophthalmoscope (SLO) image) generated by integrating tomograms. Furthermore, the analysis maps may be displayed together with at least one of the high-resolution tomogram and the original tomogram in a tile manner on the same screen. That is, the display control unit 305 corresponding to an example of the display control unit causes at least one of the number, size, and distribution of granular objects to be displayed on the display unit together with at least one of the tomogram in which a high-frequency component is combined and a tomogram acquired by the acquisition unit.

Alternatively, the number, size, and distribution of the granular objects extracted from the high-resolution tomogram may be superimposed on at least one of a high-resolution tomogram and an original tomogram and displayed. That is, the display control unit 305, which is an example of the display control unit, superimposes at least one of the number, size, and distribution of granular objects on at least one of a tomogram in which a high-frequency component is combined and a tomogram acquired by the acquisition unit and displays it on the display unit.

With the above structure, a high-resolution tomogram is displayed so as be easily viewed by the operator. This promotes better understanding of disease, allowing the tomogram to be an index of early diagnosis of disease.

Although the embodiments have been described as applied to a case using SS-OCT, the present invention is not limited thereto. The present invention is not limited to a method of image acquisition using OCT; for example, polarization sensitive (PS)-OCT using a polarization state or adaptive optics (AO)-OCT may be used.

Other Embodiments

The present invention is not limited to the above embodiments. For example, although the above embodiments use the retina of a subject eye as an image-acquisition target, an anterior eye may be used as a target. The present invention may be applied to skin etc., in addition to the subject eye.

When the structural-object emphasizing section 632 detects a granular structure, a process of adding and averaging a plurality of tomograms may be performed as pre-processing. This can reduce the possibility that speckle noise is mistaken for a granular structure to increase the resolution. This facilitates identifying a granular object in a high-resolution tomogram. The adding and averaging process is performed by, for example, the image acquisition unit 301. That is, the image acquisition unit 301 corresponds to an example of the image acquisition unit configured to acquire an averaged image by adding and averaging a plurality of tomograms acquired by the acquisition unit. The structural-object emphasizing section 632, which is an example of the first extraction unit, extracts a granular object from the averaged image.

The above embodiments are each embodied as an image processing apparatus. However, the embodiments of the present invention are not limited to the image processing apparatus. The present invention may be embodied as software running on a computer. One or more CPUs of the image processing apparatus control the entire computer using computer programs and data stored in one or more memories, such as a RAM or a ROM, to which the one or more CPUs can connect. The one or more CPUs control execution of software corresponding to the components of the image processing apparatus to implement the functions thereof.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-038923, filed Feb. 28, 2014, which is hereby incorporated by reference herein in its entirety.

The invention claimed is:

1. An image processing apparatus comprising:
an acquisition unit configured to acquire a tomogram of a subject eye obtained by B-scan;
a first extraction unit configured to extract a structural object in part of the tomogram determined according to a user operation by analyzing the tomogram;
a difference acquisition unit configured to acquire a difference image of a difference between the tomogram and a reference image obtained by scaling down a scaled-up tomogram to an original size, the scaled-up tomogram being obtained by scaling up the tomogram;
an emphasizing unit configured to perform emphasizing processing for emphasizing a portion common with the structural object over a portion not common with the structural object in the difference image; and
a combining unit configured to scale up the difference image on which the emphasizing processing is performed by the emphasizing unit to a size of the scaled-up tomogram and combine the scaled-up difference image with the scaled-up tomogram.

2. The image processing apparatus according to claim 1, wherein the first extraction unit extracts at least one of a layer boundary and a granular object as the structural object in part of the tomogram.

3. The image processing apparatus according to claim 2, further comprising:
an image acquisition unit configured to acquire an averaged image by adding and averaging a plurality of the tomograms acquired by the acquisition unit,
wherein the first extraction unit extracts the granular object from the averaged image.

4. The image processing apparatus according to claim 1, further comprising:
a second extraction unit configured to extract at least one of a layer structure and a granular object from an image combined by the combining unit.

5. The image processing apparatus according to claim 4, wherein the second extraction unit extracts at least one of a number, size, and distribution of granular objects from the image combined by the combining unit.

6. The image processing apparatus according to claim 1, further comprising:
a display control unit configured to cause the image combined by the combining unit to be displayed on a display unit.

7. The image processing apparatus according to claim 6, wherein the display control unit causes the image combined by the combining unit and the tomogram to be displayed on the display unit.

8. The image processing apparatus according to claim 7, wherein the display control unit causes the image combined by the combining unit and the tomogram to be displayed in a tiled manner on the display unit.

9. The image processing apparatus according to claim 5, further comprising:
a display control unit configured to cause at least one of a number, size, and distribution of the granular objects to be displayed on a display unit.

10. The image processing apparatus according to claim 9, wherein the display control unit causes at least a number, size, and distribution of the granular objects to be displayed on the display unit together with at least one of the image combined by the combining unit and the tomogram.

11. The image processing apparatus according to claim 10, wherein the display control unit causes at least one of a number, size, and distribution of the granular objects to be interposed on at least one of the image combined by the combining unit and the tomogram and be displayed on the display unit.

12. The image processing apparatus according to claim 1, further comprising:
an image combining unit configured to combine a plurality of images combined by the combining unit.

13. The image processing apparatus according to claim 1, wherein the tomogram acquired by the acquisition unit is a tomogram of a fundus of the subject eye.

14. A method for processing an image, comprising:
an acquisition step of acquiring a tomogram of a subject eye obtained by B-scan;
a first extraction step of extracting a structural object in part of the tomogram determined according to a user operation by analyzing the tomogram;
a difference acquisition step of acquiring a difference image of a difference between the tomogram and a reference image obtained by scaling down a scaled-up tomogram to an original size, the scaled-up tomogram being obtained by scaling up the tomogram;
an emphasizing step of performing emphasizing processing for emphasizing a portion common with the structural object over a portion not common with the structural object in the difference image;
a combining step of scaling up the difference image on which the emphasizing processing is performed in the emphasizing step to a size of the scaled-up tomogram and combining the scaled-up difference image with the scaled-up tomogram.

15. A non-transitory storage medium storing a program causing a computer to execute the steps of the image processing method according to claim 14.

16. An image processing apparatus comprising:
an acquisition unit configured to acquire a tomogram of a subject eye obtained by B-scan;

a first extraction unit configured to extract a structural object in part of the tomogram determined according to a user operation by analyzing the tomogram;

a difference acquisition unit configured to acquire a difference image of a difference between the tomogram and a reference image obtained by scaling down the tomogram and subsequently scaling up the scaled-down tomogram to an original size;

an emphasizing unit configured to perform emphasizing processing for emphasizing a portion common with the structural object over a portion not common with the structural object in the difference image; and a combining unit configured to scale up the difference image on which the emphasizing processing is performed by the emphasizing unit to a size of the scaled-up tomogram obtained by scaling up the tomogram and combine the scaled-up difference image with the tomogram.

* * * * *